(12) United States Patent
Hassan et al.

(10) Patent No.: US 8,771,605 B2
(45) Date of Patent: Jul. 8, 2014

(54) HIGH SHEAR SYSTEM FOR THE PRODUCTION OF CHLOROBENZENE

(75) Inventors: Abbas Hassan, Sugar Land, TX (US); Ebrahim Bagherzadeh, Sugar Land, TX (US); Rayford G. Anthony, College Station, TX (US); Gregory G. Borsinger, Chatham, NJ (US); Aziz Hassan, Sugar Land, TX (US)

(73) Assignee: H R D Corporation, Houston, TX (US)

( * ) Notice: Subject to any disclaimer, the term of this patent is extended or adjusted under 35 U.S.C. 154(b) by 985 days.

(21) Appl. No.: 12/751,152

(22) Filed: Mar. 31, 2010

(65) Prior Publication Data
US 2010/0183486 A1    Jul. 22, 2010

Related U.S. Application Data

(62) Division of application No. 12/137,441, filed on Jun. 11, 2008.

(60) Provisional application No. 60/946,524, filed on Jun. 27, 2007.

(51) Int. Cl.
*B01J 19/18* (2006.01)

(52) U.S. Cl.
USPC .......... 422/225; 422/215; 422/224; 422/226; 570/208; 570/207

(58) Field of Classification Search
USPC .......... 422/187, 215, 226, 225, 224; 570/208, 570/207
See application file for complete search history.

(56) References Cited

U.S. PATENT DOCUMENTS

| | | | | |
|---|---|---|---|---|
| 3,654,107 A | * | 4/1972 | Lindwall et al. | 570/190 |
| 3,781,320 A | | 12/1973 | Irwin | |
| 3,887,167 A | | 6/1975 | Irwin | |
| 3,984,484 A | * | 10/1976 | Scremin et al. | 568/749 |
| 4,329,525 A | * | 5/1982 | Riegel et al. | 570/191 |
| 4,724,269 A | | 2/1988 | Suzuki et al. | |

(Continued)

FOREIGN PATENT DOCUMENTS

| EA | 017547 | 1/2013 |
|---|---|---|
| EP | 1604969 | 12/2005 |

(Continued)

OTHER PUBLICATIONS

Chattopadhyay et al., "Understanding Mechanical Energy Driven Nonequilibrium Processing: Some Results, Eleventh International Conference on Rapidly Quenched and Metastable Materials," A Material Science and Engineering, vol. 375-377, dated Jul. 15, 2004, pp. 72-77 (9 pgs.).

(Continued)

*Primary Examiner* — Lessanework Seifu
(74) *Attorney, Agent, or Firm* — Timothy S. Westby; Porter Hedges, LLP

(57) ABSTRACT

Use of a high shear mechanical device incorporated into a process for the production of chlorobenzene is capable of decreasing mass transfer limitations, thereby enhancing the chlorobenzene production process. A system for the production of chlorobenzene from benzene and chlorine, the system comprising a reactor and an external high shear device, the outlet of which is fluidly connected to the inlet of the reactor; the high shear device capable of providing an emulsion of chlorine gas bubbles within liquid benzene.

20 Claims, 2 Drawing Sheets

(56) References Cited

U.S. PATENT DOCUMENTS

| | | | |
|---|---|---|---|
| 4,886,905 | A | 12/1989 | Larkins, Jr. |
| 4,914,029 | A | 4/1990 | Caransa et al. |
| 4,950,831 | A | 8/1990 | Staton et al. |
| 5,009,816 | A | 4/1991 | Weise et al. |
| 5,264,087 | A | 11/1993 | Lowery et al. |
| 5,382,358 | A | 1/1995 | Yeh |
| 5,451,348 | A | 9/1995 | Kingsley |
| 5,538,191 | A | 7/1996 | Holl |
| 5,710,355 | A | 1/1998 | Krishnamurti |
| 5,756,714 | A | 5/1998 | Antrim et al. |
| 5,877,350 | A | 3/1999 | Langer et al. |
| 6,194,625 | B1 | 2/2001 | Graves et al. |
| 6,251,289 | B1 | 6/2001 | Sherman |
| 6,368,366 | B1 | 4/2002 | Langer et al. |
| 6,368,367 | B1 | 4/2002 | Langer et al. |
| 6,383,237 | B1 | 5/2002 | Langer et al. |
| 6,530,964 | B2 | 3/2003 | Langer et al. |
| 6,693,213 | B1 | 2/2004 | Kolena et al. |
| 6,742,774 | B2 | 6/2004 | Holl |
| 6,768,021 | B2 | 7/2004 | Horan et al. |
| 6,787,036 | B2 | 9/2004 | Long |
| 6,809,217 | B1 | 10/2004 | Colley et al. |
| 6,827,749 | B2 | 12/2004 | Westfall et al. |
| 7,461,970 | B2 | 12/2008 | Brown |
| 7,935,840 | B2 | 5/2011 | Leveson et al. |
| 2003/0043690 | A1 | 3/2003 | Holl |
| 2004/0052158 | A1 | 3/2004 | Holl |
| 2005/0033069 | A1 | 2/2005 | Holl et al. |
| 2006/0245991 | A1 | 11/2006 | Holl |
| 2006/0272634 | A1 | 12/2006 | Nehmer et al. |
| 2009/0323458 | A1 | 12/2009 | Fischer et al. |
| 2010/0004419 | A1 | 1/2010 | Hassan et al. |

FOREIGN PATENT DOCUMENTS

| | | |
|---|---|---|
| JP | 61183235 | 8/1986 |
| JP | 2000143706 | 5/2000 |
| JP | 2002003505 | 1/2002 |
| JP | 2002121353 | 4/2002 |
| JP | 2007505201 | 3/2007 |
| WO | 9843725 | 10/1998 |
| WO | 02064708 | 8/2002 |
| WO | 2005108533 | 11/2005 |
| WO | 2007023864 | 3/2007 |

OTHER PUBLICATIONS

Office Action dated Apr. 20, 2010 for U.S. Appl. No. 12/411,660.
Office Action dated Apr. 20, 2010 for U.S. Appl. No. 12/427,286.
Office Action dated Apr. 23 for U.S. Appl. No. 12/568,155.
Office Action dated Apr. 27 for U.S. Appl. No. 12/568,280.
Office Action dated May 5, 2010 for U.S. Appl. No. 12/142,120.
Office Action dated Jun. 25, 2009 for U.S. Appl. No. 12/142,447.
Ofice Action dated Jan. 7, 2010 for U.S. Appl. No. 12/142,447.
Office Action dated May 13, 2010 for U.S. Appl. No. 12/142,447.
Office Action dated Feb. 4, 2010 for U.S. Appl. No. 12/492,721.
Office Action dated Feb. 18, 2010 for U.S. Appl. No. 12/635,433.
Office Action dated Feb. 18, 2010 for U.S. Appl. No. 12/635,454.
Office Action dated May 14, 2010 for U.S. Appl. No. 12/137,441.
Office Action dated Feb. 19, 2010 for U.S. Appl. No. 12/144,459.
Office Action dated Sep. 2, 2009 for U.S. Appl. No. 12/142,433.
Office Action dated Jan. 29, 2010 for U.S. Appl. No. 12/142,433.
Office Action dated May 24, 2010 for U.S. Appl. No. 12/142,433.
Office Action dated Apr. 30, 2010 for U.S. Appl. No. 12/141,191.
Office Action dated Oct. 27, 2009 for U.S. Appl. No. 12/142,120.
Office Action dated May 5, 2010 for U.S. Appl. No. 12/571,537.
Eurasian Office Action dated Apr. 26, 2012 for corresponding Eurasian Patent Application 2009-01294; 4 pages.
"Cavitation: A technology on the horizon," Current Science 91 (No. 1): 35-46 (2006).
IKA—Rotor—Stator Generators—2003 Processing Catalog (38 pgs.).
Office Action dated Jun. 10, 2013 for corresponding U.S. Appl. No. 12/137,441 (15 pgs.).
Daley et al., "Organic Chemistry: 18.3 Halogenation and sulfonation of benzene," dated Jul. 5, 2005 (67 pgs.).
Eurasian Office Action dated Jul. 31, 2011 for corresponding Eurasian Application No. 200901294/13 (4 pgs.).
Search Report and Written Opinion dated Aug. 28, 2008 for corresponding International Application No. PCT/US2008/066904 (4 pgs.).
Office Action dated Feb. 24, 2011 for U.S. Appl. No. 12/796,358 (13 pgs.).
Office Action dated Feb. 29, 2012 for U.S. Appl. No. 12/146,733 (8 pgs.).
Office Action dated Jun. 3, 2011 for U.S. Appl. No. 12/568,155 (11 pgs.).
Office Action dated Jun. 2, 2011 for U.S. Appl. No. 12/427,286 (12 pgs.).
Office Action dated Jun. 3, 2011 for U.S. Appl. No. 12/568,280 (16 pgs.).
Office Action dated May 14, 2010 for U.S. Appl. No. 12/137,441 (12 pgs.).
Office Action dated Oct. 6, 2010 for U.S. Appl. No. 12/137,441 (14 pgs.).
Office Action dated Feb. 17, 2011 for U.S. Appl. No. 12/137,441 (14 pgs.).
Office Action dated Jul. 21, 2011 for U.S. Appl. No. 12/137,441 (21 pgs.).
Anonymous, "Find a Mixer for your Application . . . Homogenizing-Dispersing, Suspending," URL:http://web.archive.org/web/20031004004249/http://www.ikausa.com/applications.htm, dated Oct. 4, 2003 (4 pgs.).
Anonymous, "High Shear Mixers, Homogenizers and Dispersers," Dispax Reactor by IKA, URL:http://web.archive.org/web/20030428222302/http://ikausa.com/dr.htm, dated Apr. 28, 2003 (1 pg.).
European Search Report dated Aug. 7, 2012 for corresponding European Application No. EP 08771006 (5 pgs.).
Anonymous, "Mixing Systems and Blending Systems for Continuous Blending and Mixing," URL:http://web.archive.org/web/20030425114350/http://ikausa.com/continuouse, dated Apr. 25, 2003 (1 pg.).
GCC Examination Report dated Jul. 31, 2011 for corresponding GCC Applicaiton No. GCC/P/2008/11139 (4 pgs.).
Office Action dated Dec. 27, 2013 for corresponding U.S. Appl. No. 12/137,441 (23 pgs.).

* cited by examiner

HIGH SHEAR SYSTEM FOR THE PRODUCTION OF CHLOROBENZENE

CROSS-REFERENCE TO RELATED APPLICATIONS

This application is a divisional application which claims the benefit under 35 U.S.C. §121 of U.S. patent application Ser. No. 12/137,441, filed Jun. 11, 2008, which claims the benefit under 35 U.S.C. §119(e) of U.S. Provisional Patent Application No. 60/946,524 filed Jun. 27, 2007, the disclosures of each of which are hereby incorporated herein by reference.

STATEMENT REGARDING FEDERALLY SPONSORED RESEARCH OR DEVELOPMENT

Not Applicable.

BACKGROUND OF THE INVENTION

1. Technical Field

The present disclosure relates generally to the production of chlorobenzene by chlorination of benzene and, more particularly, to apparatus and methods for producing chlorobenzene via chlorination of benzene in a high shear process. The disclosure pertains still more particularly to the reduction of mass transfer limitations for converting benzene to chlorobenzene.

2. Background of the Invention

Chlorobenzene is used as a solvent with applications in certain pesticide formulations, automotive and industrial degreasers, and as a chemical intermediate to make herbicides, rubber and dyes. Benzene reacts with chlorine in the presence of a catalyst at room temperature, replacing one of the hydrogen atoms on the benzene ring with a chlorine atom. The catalyst is typically aluminum chloride or iron.

Iron is altered during the reaction such that chlorine forms iron (III) chloride, $FeCl_3$.

$$2Fe + 3Cl_2 \rightarrow 2FeCl_3. \quad (1)$$

This compound acts as the catalyst and behaves like aluminum chloride, $AlCl_3$, in the reaction. The reaction between benzene and chlorine in the presence of either aluminum chloride or iron gives chlorobenzene, or, written more compactly:

$$C_6H_6 + Cl_2 \rightarrow C_6H_5Cl + HCl. \quad (2)$$

$$C_6H_5 + Cl_2 \rightarrow C_6H_4Cl + HCl. \quad (3)$$

$$C_6H_4Cl + Cl_2 \rightarrow C_6H_3Cl + HCl. \quad (4)$$

As reaction (2) is the desired reaction, certain parameters must be maintained in the reactor. In certain cases, dichlorobenzene can be formed if reaction temperatures are not controlled properly.

There is a need in the industry for improved methods of producing chlorobenzene from benzene and chlorine whereby capital and/or operating costs are reduced via operation at lower temperature and/or pressure, product yield is increased and/or reaction time is decreased.

SUMMARY

A high shear system and method for accelerating the production of chlorobenzene are disclosed. The disclosed high shear method reduces mass transfer limitations, thereby improving reaction conditions in the reactor such as the reaction rate, temperature, pressure, contact time, and/or product yield. In accordance with certain embodiments of the present disclosure, a method is provided that enhances the rate of a liquid phase process for the production of chlorobenzene from benzene by providing for more optimal time, temperature and/or pressure conditions than are currently used. The method employs a high shear mechanical device to provide enhanced time, temperature, and pressure conditions resulting in accelerated chemical reactions between multiphase reactants. In an embodiment, the method comprises the use of a pressurized high shear device to provide for production of chlorobenzene without the need for large volume reactors.

According to an embodiment, herein disclosed is a method for producing chlorobenzene by obtaining a high shear device having at least one rotor/stator set configured for producing a tip speed of at least 5 m/s, wherein the high shear device comprises at least one rotor and at least on stator; forming an emulsion of benzene and chlorine gas; wherein the benzene comprises a pressurized liquid solution, and the chlorine gas comprises bubbles in the emulsion with a mean diameter of less than about 5 μm; introducing the emulsion into a reactor comprising a catalyst; and reacting the emulsion at a temperature less than about 40° C. in the reactor, from which a product comprising chlorobenzene is removed. The pressurized benzene solution can be pressurized to at least about 203 kPa. The chlorine gas bubbles can have an average diameter of less than about 1.5 μm. In embodiments, the high shear device has a tip speed of at least about 5 m/s. In embodiments, the high shear device produces a localized pressure of about 1000 MPa at the tip. In embodiments, forming the emulsion comprises subjecting the chlorine gas bubbles and pressurized benzene solution to a shear rate of greater than about 20,000 s$^{-1}$. In embodiments, forming the emulsion comprises an energy expenditure of at least 1000 W/m$^3$. The emulsion can comprise a micro-foam. In embodiments, the catalyst comprises at least one catalyst selected from the group consisting of Lewis acids, metallic chlorides, iodine and combinations thereof. The method can further comprise distilling the product at least once to remove the chlorobenzene.

Also disclosed herein is a method for producing chlorobenzene by forming an emulsion of chlorine gas bubbles in aqueous solution comprising benzene by introducing liquid benzene and chlorine gas into a high shear device and subjecting the mixture of liquid benzene and chlorine gas to a shear rate of at least 20,000 s$^{-1}$. The high shear device can comprise at least one rotor and at least one stator.

Also disclosed herein is a system for the production of chlorobenzene, the system comprising a high shear device configured to produce a dispersion comprising chlorine gas bubbles having an average bubble diameter of less than about 5 μm; a pump positioned upstream of the high shear device and configured to provide an inlet stream comprising chlorine gas and liquid benzene thereto; and a reactor from which a product comprising chlorobenzene is removed, wherein the reactor is fluidly connected to an outlet of the high shear device such that the dispersion may be introduced thereto. The high shear device can comprise at least one rotor and at least one complementarily-shaped stator. In embodiments, the high shear device is operable to produce a tip speed at a tip of the at least one rotor of at least about 5 m/s. In embodiments, the high shear device is operable to produce a tip speed at a tip of the at least one rotor of at least about 23 m/s. In embodiments, the high shear device is operable to produce a tip speed at a tip of the at least one rotor of at least about 40 m/s. In embodiments, the high shear device produces a localized pressure of at least about 1000 MPa at the tip of the at least one rotor during operation. In embodiments, the high shear device is operable to subject the contents therein to a shear rate of greater than about 20,000 s$^{-1}$. In embodiments, the high shear device exhibits an energy expenditure of at least 1000 W/m$^3$ during operation. In embodiments, the dispersion comprises a micro-foam. In embodiments, the reactor is maintained at a temperature of less than about 40° C. In embodiments, the high shear device comprises at least two generators, each generator comprising a rotor and a complementarily-shaped stator. The high shear device can be external to the reactor.

The system can further comprise at least one distillation column downstream of the reactor, the distillation column configured to separate unreacted benzene from a chlorobenzene product. In embodiments, the at least one distillation column is fluidly connected to the pump, whereby unreacted benzene may be recycled to the high shear device. The system can further comprise a dispersible chlorine gas inlet upstream of the high shear device and downstream of the pump. The system can further comprise an inlet line whereby a catalyst may be introduced into the system. In embodiments, the catalyst is selected from the group consisting of Lewis acids, metallic chlorides, iodine and combinations thereof. In embodiments, the pump provides the inlet stream at a pressure of least about 203 kPa. In embodiments, the dispersion comprises chlorine gas bubbles having an average diameter of less than about 1.5 µm. In embodiments, the dispersion comprises chlorine gas bubbles having an average diameter on the submicron scale.

These and other embodiments, features, and advantages will be apparent in the following detailed description and drawings.

BRIEF DESCRIPTION OF THE DRAWINGS

For a more detailed description of the preferred embodiment of the present invention, reference will now be made to the accompanying drawings, wherein.

DETAILED DESCRIPTION

Overview

Figure 1:
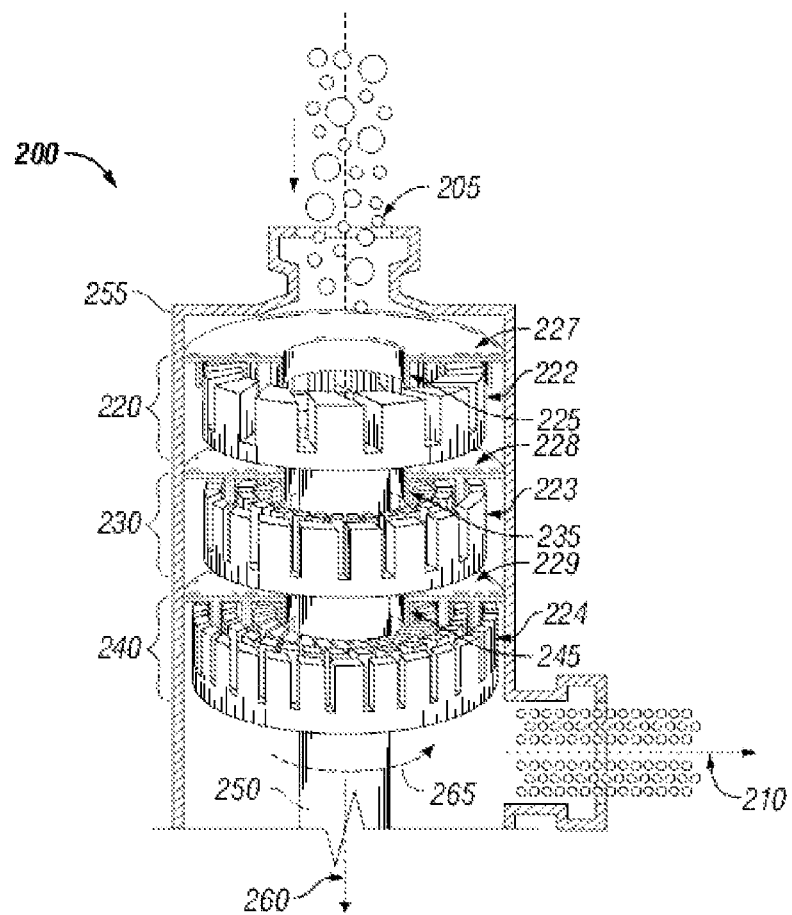
FIG. 1 is a cross-sectional diagram of a high shear device for the production of chlorobenzene.

A system and method employ an external high shear mechanical device to provide rapid contact and mixing of chemical ingredients in a controlled environment in the reactor/mixer device. The high shear device reduces the mass transfer limitations on the reaction and thus increases the overall reaction rate.

Chemical reactions involving liquids, gases and solids rely on the laws of kinetics that involve time, temperature, and pressure to define the rate of reactions. In cases where it is desirable to react two or more raw materials of different phases (e.g. solid and liquid; liquid and gas; solid, liquid and gas), one of the limiting factors in controlling the rate of reaction involves the contact time of the reactants. In the case of heterogeneously catalyzed reactions there may be the additional rate limiting factor of having the reaction products removed from the surface of the catalyst to enable the catalyst to catalyze further reactants.

In conventional reactors, contact time for the reactants and/or catalyst is often controlled by mixing which provides contact between two or more reactants involved in a chemical reaction. A reactor assembly that comprises an external high shear mixer makes possible decreased mass transfer limitations and thereby allows the reaction to more closely approach kinetic limitations. When reaction rates are accelerated, residence times may be decreased, thereby increasing obtainable throughput. Alternatively, where the current yield is acceptable, decreasing the required residence time allows for the use of lower temperatures and/or pressures than conventional processes.

High Shear Device.

High shear devices (HSD) such as a high shear mixer, or high shear mill, are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid particles. The classes are distinguished based on delivered energy density. There are three classes of industrial mixers having sufficient energy density to consistently produce mixtures or emulsions with particle or bubble sizes in the range of 0 to 50 µm.

Homogenization valve systems are typically classified as high energy devices. Fluid to be processed is pumped under very high pressure through a narrow-gap valve into a lower pressure environment. The pressure gradients across the valve and the resulting turbulence and cavitations act to break-up any particles in the fluid. These valve systems are most commonly used in milk homogenization and can yield average particle size range from about 0.01 µm to about 1 µm. At the other end of the spectrum are high shear mixer systems classified as low energy devices. These systems usually have paddles or fluid rotors that turn at high speed in a reservoir of fluid to be processed, which in many of the more common applications is a food product. These systems are usually used when average particle, globule or bubble, sizes of greater than 20 microns are acceptable in the processed fluid.

Between low energy-high shear mixers and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely-controlled rotor-stator gap, which is maybe between 0.025 mm and 10.0 mm. Rotors are usually driven by an electric motor through a direct drive or belt mechanism. Many colloid mills, with proper adjustment, can achieve average particle, or bubble, sizes of about 0.01 µm to about 25 µm in the processed fluid. These capabilities render colloid mills appropriate for a variety of applications including colloid and oil/water-based emulsion processing such as that required for cosmetics, mayonnaise, silicone/silver amalgam formation, or roofing-tar mixing.

Referring now to FIG. 1, there is presented a schematic diagram of a high shear device 200. High shear device 200 comprises at least one rotor-stator combination. The rotor-stator combinations may also be known as generators 220, 230, 240 or stages without limitation. The high shear device 200 comprises at least two generators, and most preferably, the high shear device comprises at least three generators.

The first generator 220 comprises rotor 222 and stator 227. The second generator 230 comprises rotor 223, and stator 228; the third generator comprises rotor 224 and stator 229. For each generator 220, 230, 240 the rotor is rotatably driven by input 250. The generators 220, 230, 240 rotate about axis 260 in rotational direction 265. Stator 227 is fixably coupled to the high shear device wall 255.

The generators include gaps between the rotor and the stator. The first generator 220 comprises a first gap 225; the second generator 230 comprises a second gap 235; and the third generator 240 comprises a third gap 245. The gaps 225, 235, 245 are between about 0.025 mm (0.01 in) and 10.0 mm (0.4 in) wide. Alternatively, the process comprises utilization of a high shear device 200 wherein the gaps 225, 235, 245 are between about 0.5 mm (0.02 in) and about 2.5 mm (0.1 in). In certain instances the gap is maintained at about 1.5 mm (0.06 in). Alternatively, the gaps 225, 235, 245 are different between generators 220, 230, 240. In certain instances, the gap 225 for the first generator 220 is greater than about the gap 235 for the second generator 230, which is greater than about the gap 245 for the third generator 240.

Additionally, the width of the gaps 225, 235, 245 may comprise a coarse, medium, fine, and super-fine characterization. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. Stators 227, 228, and 229 may comprise a number of stator teeth circumferentially spaced about the circumference of each stator. In embodiments, the inner diameter of the rotor is about 11.8 cm. In embodiments, the outer diameter of the stator is about 15.4 cm. In further embodiments, the rotor and stator may have an outer diameter of about 60 mm for the rotor, and about 64 mm for the stator. Alternatively, the rotor and stator may have alternate diameters in order to alter the tip speed and shear pressures. In certain embodiments, each of three stages is operated with a super-fine generator, comprising a gap of between about 0.025 mm and about 3 mm. When a feed stream 205 including solid particles is to be sent through high shear device 200, the appropriate gap width is first selected for an appropriate reduction in particle size and increase in particle surface area. In embodiments, this is beneficial for increasing catalyst surface area by shearing and dispersing the particles.

High shear device 200 is fed a reaction mixture comprising the feed stream 205. Feed stream 205 comprises an emulsion of the dispersible phase and the continuous phase. Emulsion refers to a liquefied mixture that contains two distinguishable substances (or phases) that will not readily mix and dissolve together. Most emulsions have a continuous phase (or matrix), which holds therein discontinuous droplets, bubbles, and/or particles of the other phase or substance. Emulsions may be highly viscous, such as slurries or pastes, or may be foams, with tiny gas bubbles suspended in a liquid. As used herein, the term "emulsion" encompasses continuous phases comprising gas bubbles, continuous phases comprising particles (e.g., solid catalyst), continuous phases comprising droplets of a fluid that is substantially insoluble in the continuous phase, and combinations thereof.

Feed stream 205 may include a particulate solid catalyst component. Feed stream 205 is pumped through the generators 220, 230, 240, such that product dispersion 210 is formed. In each generator, the rotors 222, 223, 224 rotate at high speed relative to the fixed stators 227, 228, 229. The rotation of the rotors pumps fluid, such as the feed stream 205, between the outer surface of the rotor 222 and the inner surface of the stator 227 creating a localized high shear condition. The gaps 225, 235, 245 generate high shear forces that process the feed stream 205. The high shear forces between the rotor and stator functions to process the feed stream 205 to create the product dispersion 210. Each generator 220, 230, 240 of the high shear device 200 has interchangeable rotor-stator combinations for producing a narrow distribution of the desired bubble size, if feedstream 205 comprises a gas, or globule size, if feedstream 205 comprises a liquid, in the product dispersion 210.

The product dispersion 210 of gas particles, or bubbles, in a liquid comprises an emulsion. In embodiments, the product dispersion 210 may comprise a dispersion of a previously immiscible or insoluble gas, liquid or solid into the continuous phase. The product dispersion 210 has an average gas particle, or bubble, size less than about 1.5 µm; preferably the bubbles are sub-micron in diameter. In certain instances, the average bubble size is in the range from about 1 µm to about 1.0 µm. Alternatively, the average bubble size is less than about 400 nm (0.4 µm) and most preferably less than about 100 nm (0.1 µm).

Tip speed is the velocity (m/s) associated with the end of one or more revolving elements that is transmitting energy to the reactants. Tip speed, for a rotating element, is the circumferential distance traveled by the tip of the rotor per unit of time, and is generally defined by the equation $V$ (m/s)$=\pi \cdot D \cdot n$, where V is the tip speed, D is the diameter of the rotor, in meters, and n is the rotational speed of the rotor, in revolutions per second. Tip speed is thus a function of the rotor diameter and the rotation rate.

For colloid mills, typical tip speeds are in excess of 23 m/s (4500 ft/min) and can exceed 40 m/s (7900 ft/min). For the purpose of the present disclosure the term 'high shear' refers to mechanical rotor-stator devices, such as mills or mixers, that are capable of tip speeds in excess of 5 m/s (1000 ft/min) and require an external mechanically driven power device to drive energy into the stream of products to be reacted. A high shear device combines high tip speeds with a very small shear gap to produce significant friction on the material being processed. Accordingly, a local pressure in the range of about 1000 MPa (about 145,000 psi) to about 1050 MPa (152, 300 psi) and elevated temperatures at the tip of the shear mixer are produced during operation. In certain embodiments, the local pressure is at least about 1034 MPa (about 150,000 psi). The local pressure further depends on the tip speed, fluid viscosity, and the rotor-stator gap during operation.

An approximation of energy input into the fluid (kW/l/min) can be made by measuring the motor energy (kW) and fluid output (l/min). In embodiments, the energy expenditure of a high shear device is greater than 1000 W/m$^3$. In embodiments, the energy expenditure is in the range of from about 3000 W/m$^3$ to about 7500 W/m$^3$. The high shear device 200 combines high tip speeds with a very small shear gap to produce significant shear on the material. The amount of shear is typically dependent on the viscosity of the fluid. The shear rate generated in a high shear device 200 may be greater than 20,000 s$^{-1}$. In embodiments, the shear rate generated is in the range of from 20,000 s$^{-1}$ to 100,000 s$^{-1}$.

The high shear device 200 produces a gas emulsion capable of remaining dispersed at atmospheric pressure for at least about 15 minutes. For the purpose of this disclosure, an emulsion of gas particles, or bubbles, in the dispersed phase in product dispersion 210 that are less than 1.5 µm in diameter may comprise a micro-foam. Not to be limited by a specific theory, it is known in emulsion chemistry that sub-micron particles, or bubbles, dispersed in a liquid undergo movement primarily through Brownian motion effects. The bubbles in the emulsion of product dispersion 210 created by the high shear device 200 may have greater mobility through boundary layers of solid catalyst particles, thereby facilitating and accelerating the catalytic reaction through enhanced transport of reactants.

The rotor is set to rotate at a speed commensurate with the diameter of the rotor and the desired tip speed as described hereinabove. Transport resistance is reduced by incorporation of high shear device 200 such that the velocity of the reaction is increased by at least about 5%. Alternatively, the high shear device 200 comprises a high shear colloid mill that serves as an accelerated rate reactor. The accelerated rate reactor comprises a single stage dispersing chamber. The accelerated rate reactor comprises a multiple stage inline disperser comprising at least 2 stages.

Selection of the high shear device 200 is dependent on throughput requirements and desired particle or bubble size in the outlet dispersion 210. In certain instances, high shear device 200 comprises a DISPAX® Reactor of IKA® Works, Inc. Wilmington, N.C. and APV North America, Inc. Wilmington, Mass. Model DR 2000/4, for example, comprises a belt drive, 4M generator, PTFE sealing ring, inlet flange 1" sanitary clamp, outlet flange ¾" sanitary clamp, 2HP power, output speed of 7900 rpm, flow capacity (water) approximately 300 l/h to approximately 700 l/h (depending on generator), a tip speed of from 9.4 m/s to about 41 m/s (about 1850 ft/min to about 8070 ft/min). Several alternative models are available having various inlet/outlet connections, horsepower, tip speeds, output rpm, and flow rate.

Without wishing to be limited to a particular theory, it is believed that the level or degree of high shear mixing is sufficient to increase rates of mass transfer and may also produce localized non-ideal conditions that enable reactions to occur that would not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," Current Science 91 (No. 1): 35-46 (2006). The high shear mixing device of certain embodiments of the present system and methods is operated under what are believed to be cavitation conditions effective to dissociate the benzene into free radicals exposed to chlorination catalysts for the formation of the chlorobenzene product.

Description of High Shear Chlorobenzene Production Process and System.

Figure 2:
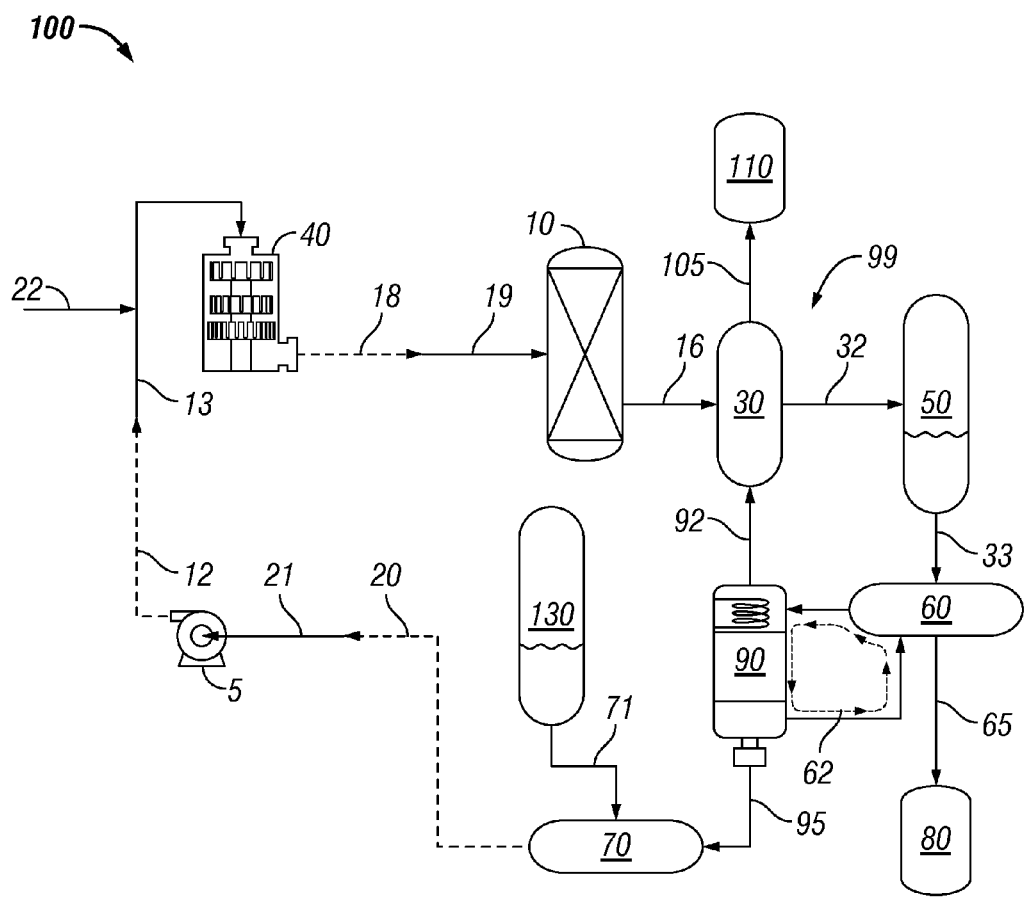
FIG. 2 is a process flow diagram according to an embodiment of the present disclosure including a high shear device for production of chlorobenzene.

The high shear chlorobenzene production process and system of the present disclosure will now be described in relation to FIG. 2 which is a representative process flow diagram of a high shear system (HSS) 100 for the production of chlorobenzene from benzene and chlorine gas. FIG. 2 illustrates the basic components of a representative high shear chlorobenzene production system. These components comprise pump 5, high shear mixer 40, and reactor 10.

Pump 5 is used to provide a controlled flow throughout high shear device (HSD) 40 and high shear system 100 for chlorobenzene production. Pump inlet stream 21 comprises liquid benzene for introduction to pump 5. In certain embodiments, pump inlet stream 21 comprises dry benzene. Pump 5 increases the pressure of the pump inlet stream 21 to greater than about 203 kPa (about 2 atm); alternatively, the inlet stream 21 is pressurized to greater than about 304 kPa (about 3 atm). Additionally, pump 5 may build pressure throughout HSS 100. In this way, HSS 100 combines high shear with pressure to enhance reactant intimate mixing. Preferably, all contact parts of pump 5 are stainless steel, for example, 316 stainless steel. Pump 5 may be any suitable pump, for example, a Dayton Pressure Booster Pump Model 2P372E, Dayton Electric Co (Niles, Ill.).

The pressurized benzene liquid exits pump 5 via pump exit stream 12. Pump exit stream 12 is in fluid communication with HSD inlet stream 13. In certain instances, dispersible gas stream 22 comprising chlorine gas is introduced or injected to HSD inlet stream 13. In some embodiments chlorine gas may continuously be fed into exit stream 12 to form HSD inlet stream 13. HSD inlet stream 13 comprises a mixture of chlorine gas and catalyst in liquid benzene. Dispersible gas stream 22 and pressurized pump exit stream 12 may be injected separately into HSD inlet stream 13 for processing by high shear device 40. Furthermore, any suitable chlorination catalyst known to those of skill in the art may be introduced into HSD inlet stream 13 for processing by HSD 40. In certain instances, the catalyst introduced comprises a Lewis acid catalyst. The catalyst may be chosen from metallic chlorides and iodine. In embodiments, the catalyst is selected from Lewis acids selected from the group consisting of Fe, $FeCl_3$ and $AlCl_3$. HSD inlet stream 13 is in fluid communication with the high shear device 40.

HSD 40 serves to intimately mix the liquid benzene solution with dispersible gas stream 22 and the catalyst. As discussed in detail above, high shear device 40 is a mechanical device that utilizes, for example, a stator rotor mixing head with a fixed gap between the stator and rotor. In high shear device 40, chlorine gas and benzene are mixed to form an emulsion comprising microbubbles and nanobubbles of chlorine gas. In embodiments, the resultant dispersion comprises bubbles in the submicron size. In embodiments, the resultant dispersion has an average bubble size less than about 1.5 µm. In embodiments, the mean bubble size is less than from about 0.1 µm to about 1.5 µm. Not to be limited by a specific method, it is known in emulsion chemistry that submicron particles dispersed in a liquid undergo movement primarily through Brownian motion effects. Thus it is believed that submicron gas particles created by the high shear device 40 have greater mobility through boundary layers of solid catalyst particles thereby facilitating and accelerating the catalytic reaction through greater transport of reactants. In embodiments, the high shear mixing produces gas bubbles capable of remaining dispersed at atmospheric pressure for about 15 minutes or longer depending on the bubble size. In embodiments, the mean bubble size is less than about 400 nm; more preferably, less than about 100 nm. HSD 40 serves to create an emulsion of chlorine bubbles within high shear inlet stream 13 comprising liquid benzene and chlorine gas. The emulsion may further comprise a micro-foam.

The emulsion exits HSD 40 by the HSD emulsion stream 18. The HSD emulsion stream 18 may undergo further processing prior to introduction to the reactor 10. Before introduction to reactor 10, the moisture content of benzene may be reduced. In certain embodiments, the benzene in HSD emulsion stream 18 comprises dry benzene. HSD emulsion stream 18 is introduced into reactor 10 by reactor inlet stream 19. Reactor inlet stream 19 is in fluid communication with reactor 10.

Forming the emulsion in the presence of a catalyst may initiate the reaction process of chlorination. Chlorination reactions will occur whenever suitable time temperature and pressure conditions exist. In instances where a slurry based catalyst is utilized, reaction is more likely to occur at points outside reactor 10. In this sense chlorination could occur at any point in the flow diagram of FIG. 2 where temperature and pressure conditions are suitable for the reaction. Nonetheless a discrete reactor 10 is often desirable to allow for increased residence time, agitation and heating and/or cooling. In fixed bed catalyst applications, the catalyst increases the rate of the chlorination reaction.

Reactor 10 is configured for chlorobenzene production. Reactor 10 may further comprise temperature control (i.e. heat exchanger), stirring system, and level regulator as known to those of skill in the art. In embodiments, inlet stream 15 is fluidly coupled to reactor 10. Inlet stream 15 may comprise additional catalyst for catalyzing the chlorination of benzene to chlorobenzene. As described herein, a Lewis acid may be added to promote the production of chlorobenzene. In certain embodiments, in reactor 10, chlorine gas reacts with dry benzene utilizing a Lewis acid catalyst at a predetermined temperature to yield chlorobenzene mixtures. In embodiments, chlorobenzene production is continuous within the reactor. Reactor 10 is drained by product stream 16.

A specified reaction temperature may be maintained in the reactor 10, as known to those of skill in the art. In certain embodiments, the reactor includes internally or externally positioned heat exchangers. Alternatively, heat exchangers may be positioned in any location along the production stream within HSS 100. Suitable locations for external heat transfer devices include between pump 5 and high shear mixer 40, between high shear mixer 40 and reactor 10, and between reactor 10 and further processing systems. There are many types of heat transfer devices that may be suitable; such exchangers may include shell and tube, plate, and coil heat exchangers without limitation. Further heat exchangers may be known to one skilled in the art.

The chlorination product stream 16 comprises chlorobenzene, unconverted benzene, and HCl. Product stream 16 may be treated by any means known in the art to recover any unreacted benzene, remove produced hydrochloric acid (HCl), and purify chlorinated benzene. In an embodiment illustrated in FIG. 2, product stream 16 is fluidly coupled with a treatment system 99. Treatment system 99 comprises treatment vessel 30; treatment vessel 30 is fluidly coupled to reactor 10 by product stream 16. Further, treatment vessel 30 is drained by catalyst free stream 32 to a holding tank 50. Holding tank 50 stores the catalyst free chlorobenzene product prior to further treatment. In the illustrated embodiment, holding tank 50 is in fluid communication with a chlorobenzene distillation column(s) 60 via distillation inlet stream 33. The chlorobenzene distillation column(s) 60 are in fluid connection with further processing streams 80 by the chlorobenzene stream 65. Chlorobenzene distillation column(s) 60 may be further in communication with a reflux drum 90, by gas recycle system 62. Gas recycle system 62 is fluid communication between reflux drum 90 and chlorobenzene distillation column(s) 60. In certain instances, reflux drum 90 is fluidly coupled to treatment vessel 30 by water stream 92. Reflux drum 90 additionally comprises recovered benzene stream 95 in fluid communication with secondary distillation column(s) 70. Secondary distillation column(s) 70 may drain benzene holding tank 130 via stream 71 to feed recycle stream 20. Recycle stream 20 is fluidly coupled to pump inlet stream 21.

Treatment vessel 30 comprises a tank, vessel, or container configured for acid and catalyst removal. In embodiments, the acid and catalyst from product stream 16 are removed with water before introduction to holding tank 50. The products comprising chlorobenzene from holding tank 50 are fed into chlorobenzene distillation column(s) 60 via distillation inlet line 33. Chlorobenzene stream 65 is removed for further processing into final products such as rubber, dyes, pesticides, and the like, without limitation. Alternatively, chlorobenzene stream 65 may be sent for further separation, for example to a distillation column wherein monochlorobenzene may be separated from other chlorobenzene isomers, such as paradichlorobenzene, orthodichlorobenzene, and trichlorobenzene.

In certain embodiments, treatment vessel 30 is in fluid communication with solvent recovery system 110. Water is drained from treatment vessel 30, with dissolved acids and catalyst, and is sent via stream 105 to the solvent recovery system 110 for further removal of the organics from the water.

Benzene-containing vapor in the gas recycle system 62 is directed from distillation column 60, condensed, and sent to reflux drum 90. In embodiments, a portion of benzene from reflux drum 90 is recycled to distillation column(s) 60 by gas recycle system 62. Water stream 92 may be removed from reflux drum 90 for return to treatment vessel 30 and/or continuing processing by solvent recovery system 110. A portion of recovered benzene stream 95, from reflux drum 90, may be supplemented by wet benzene from holding tank 130. The stream 71 is sent to secondary distillation column(s) 70 with recovered benzene stream 95 to produce dry benzene. The dry benzene makes up recycle stream 20, and may be injected into pump inlet stream 21 for recycling through high shear system 100 comprising high shear device 40.

In embodiments, use of the disclosed process comprising reactant mixing via high shear device 40 allows greater conversion of benzene to chlorobenzene and/or an increase in throughput. In embodiments, there may be several high shear devices 40 used in series. In embodiments, the method comprises incorporating high shear device 40 into an established process thereby enabling the increase in production (greater throughput) from a process operated without high shear device 40. The superior dissolution provided by the high shear mixing may allow improvements in operating conditions such as temperature, pressure, and contact time while maintaining, or increasing, reaction rate. In embodiments, the method and system of this disclosure enable design of a smaller and/or less capital intensive process than previously possible without the incorporation of external high shear mixer 40. In embodiments, the disclosed method reduces operating costs/increases production from an existing process. Alternatively, the disclosed method may reduce capital costs for the design of new processes. Potential benefits of this modified system and method for the production of chlorobenzene include, but are not limited to, faster cycle times, increased throughput, reduced operating costs, and/or reduced capital expense due to the possibility of designing smaller reactors and/or operating the chlorobenzene production at lower temperature and/or pressure.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Description of Related Art is not an admission that it is prior art to the present invention, especially any reference that may have a publication date after the priority date of this application. The disclosures of all patents, patent applications, and publications cited herein are hereby incorporated by reference, to the extent they provide exemplary, procedural or other details supplementary to those set forth herein.

We claim:

1. A system for the production of chlorobenzene, the system comprising:
   a high shear device configured to produce a dispersion comprising chlorine gas bubbles having an average bubble diameter of less than about 5 μm in liquid benzene;
   a pump positioned upstream of the high shear device and configured to provide an inlet stream comprising chlorine gas and liquid benzene thereto;
   a reactor from which a reactor product comprising chlorobenzene, byproduct hydrochloric acid, and unreacted benzene is removed, wherein the reactor is fluidly connected to an outlet of the high shear device such that the dispersion may be introduced thereto; and
   a treatment vessel fluidly connected with the reactor, whereby the reactor product may be introduced thereto, the treatment vessel configured to remove hydrochloric acid from the reactor product via contact thereof with a water stream, thus providing an aqueous hydrochloric acid stream, and a treatment vessel product comprising chlorobenzene and unreacted benzene.

2. The system of claim 1 wherein the high shear device comprises at least one rotor and at least one complementarily-shaped stator.

3. The system of claim 2 wherein the high shear device is operable to produce a tip speed at a tip of the at least one rotor of at least about 5 m/s.

4. The system of claim 2 wherein the high shear device is operable to produce a tip speed at a tip of the at least one rotor of at least about 23 m/s.

5. The system of claim 2 wherein the high shear device is operable to produce a tip speed at a tip of the at least one rotor of at least about 40 m/s.

6. The system of claim 2 wherein the high shear device produces a localized pressure of at least about 1000 MPa at a tip of the at least one rotor during operation.

7. The system of claim 1 wherein the high shear device is operable to subject the contents therein to a shear rate of greater than about 20,000 $s^{-1}$.

8. The system of claim 1 wherein the high shear device exhibits an energy expenditure of at least 1000 $W/m^3$ during operation.

9. The system of claim 1 wherein the high shear device is configured to produce a dispersion comprising a micro-foam.

10. The system of claim 1 further comprising heat transfer apparatus configured to maintain the reactor at a temperature of less than about 40° C.

11. The system of claim 1 wherein the high shear device comprises at least two generators, each generator comprising a rotor and a complementarily-shaped stator.

12. The system of claim 1 wherein the high shear device is external to the reactor.

13. The system of claim 1 further comprising at least one distillation column downstream of the treatment vessel, wherein the distillation column is configured to separate unreacted benzene from the treatment vessel product.

14. The system of claim 13 wherein the at least one distillation column is fluidly connected to the pump, whereby unreacted benzene may be recycled to the high shear device.

15. The system of claim 1 further comprising a dispersible chlorine gas inlet upstream of the high shear device and downstream of the pump.

16. The system of claim 1 further comprising an inlet line whereby a catalyst may be introduced into the system.

17. The system of claim 16 wherein the catalyst is selected from the group consisting of Lewis acids, metallic chlorides, iodine and combinations thereof.

18. The system of claim 1 wherein the pump provides the inlet stream at a pressure of least about 203 kPa.

19. The system of claim 1 wherein the high shear device is configured to produce a dispersion comprising chlorine gas bubbles having an average bubble diameter of less than about 1.5 μm in liquid benzene.

20. The system of claim 1 wherein the high shear device is configured to provide a dispersion comprising chlorine gas bubbles having an average bubble diameter on the submicron scale in liquid benzene.

* * * * *